(12) United States Patent
Howell et al.

(10) Patent No.: US 11,365,440 B2
(45) Date of Patent: Jun. 21, 2022

(54) METHOD FOR PROCESSING ROLLING CIRCLE AMPLIFICATION PRODUCTS

(71) Applicant: Vanadis Diagnostics, Sollentuna (SE)

(72) Inventors: Mathias Howell, Uppsala (SE); Ove Öhman, Uppsala (SE); Fredrik Persson, Uppsala (SE); Linus Olausson, Uppsala (SE)

(73) Assignee: VANADIS DIAGNOSTICS, Sollentuna (SE)

( * ) Notice: Subject to any disclaimer, the term of this patent is extended or adjusted under 35 U.S.C. 154(b) by 0 days.

(21) Appl. No.: 16/987,283

(22) Filed: Aug. 6, 2020

(65) Prior Publication Data
US 2020/0362388 A1 Nov. 19, 2020

Related U.S. Application Data

(62) Division of application No. 15/724,573, filed on Oct. 4, 2017, now Pat. No. 10,781,476.

(60) Provisional application No. 62/413,762, filed on Oct. 27, 2016.

(51) Int. Cl.
| | |
|---|---|
| *C12Q 1/68* | (2018.01) |
| *C12Q 1/682* | (2018.01) |
| *C12Q 1/6851* | (2018.01) |
| *B01J 13/04* | (2006.01) |
| *C08L 83/04* | (2006.01) |
| *G01N 33/58* | (2006.01) |

(52) U.S. Cl.
CPC .............. *C12Q 1/682* (2013.01); *B01J 13/04* (2013.01); *C08L 83/04* (2013.01); *C12Q 1/6851* (2013.01); *G01N 33/582* (2013.01); *G01N 33/586* (2013.01); *C08L 2201/10* (2013.01)

(58) Field of Classification Search
None
See application file for complete search history.

(56) References Cited

U.S. PATENT DOCUMENTS

| | | | |
|---|---|---|---|
| 5,854,033 A | 12/1998 | Lizardi | |
| 2003/0096268 A1 | 5/2003 | Weiner et al. | |
| 2005/0009022 A1* | 1/2005 | Weiner ................. | B01J 19/0046 435/6.12 |
| 2006/0134397 A1 | 6/2006 | Smith | |
| 2006/0228813 A1 | 10/2006 | Wu et al. | |
| 2010/0047773 A1 | 2/2010 | Koch et al. | |
| 2013/0323729 A1 | 12/2013 | Landegren et al. | |

FOREIGN PATENT DOCUMENTS

| | | |
|---|---|---|
| CN | 102827929 | 6/2014 |
| RU | 2116349 C1 | 7/1998 |
| WO | 2006098696 | 9/2006 |
| WO | 2006098696 A1 | 9/2006 |
| WO | WO-2006098696 A1 * | 9/2006 ........ B01L 3/502707 |
| WO | 2011142836 | 11/2011 |
| WO | 2012019200 | 2/2012 |
| WO | 2015083001 | 6/2015 |
| WO | 2015083002 | 6/2015 |
| WO | 2016/174649 | 11/2016 |

OTHER PUBLICATIONS

Durtschi et al., "Increased sensitivity of bacterial detection in cerebrospinal fluid by fluorescent staining on low-fluorescence membrane filters" Journal of Medical Microbiology, 2005, pp. 843-850, vol. 54.
Ingham et al., "Where bio meets nano: The many uses for nanoporous aluminum oxide in biotechnology" Biotechnology Advances, 2012, pp. 1089-1099, vol. 30.
Poinern et al., "Progress in Nano-Engineered Anodic Aluminum Oxide Membrane Development" Materials, 2011, pp. 487-526, vol. 4.
Santos et al., "Nanoporous anodic aluminum oxide for chemical sensing and biosensors" Trends in Analytical Chemistry, Mar. 2013, p. 25-38, vol. 44.
Tanaka et al., "Single-Molecule DNA Patterning and Detection by Padlock Probing and Rolling Circle Amplification in Microchannels for Analysis of Small Sample Volumes" Analytical Chemistry, 2011, pp. 3352-3357, vol. 83.
Van Beuningen et al., "Fast and Specific Hybridization Using Flow-Through Microarrays on Porous Metal Oxide" Clinical Chemistry, 2001, pp. 1931-1933, vol. 47.
Wang et al., "Detection of genetically modified crops using multiplex asymmetric polymerase chain reaction and asymmetric hyperbranched rolling circle amplification coupled with reverse dot blot", Food Chemistry, 2014, 173: 1022-1029.
Reiss et al., "Synthesis and Stretching of Rolling Circle Amplification Products in a Flow-Through System", Small, 2009, 5(20): 2316-2322.
Blau, "Prospects for Neuroprosthetics: Flexible Microelectrode Arrays with Polymer Conductors", Applied Biomedical Engineering, 2011, Chapter 5, p. 83-122.
Nolte et al., "Filled Microcavity Arrays Produced by Polyelectrolyte Multilayer Membrane Transfer", Advanced Materials, 2005, 17: 1665-1669.
Smolina et al., "High-density fluorescently labeled rolling-circle amplicons for DNA diagnostics", Analytical Biochemistry, 2005; 347: 152-155.

* cited by examiner

*Primary Examiner* — Stephanie K Mummert
(74) *Attorney, Agent, or Firm* — James S. Keddie; Bozicevic, Field & Francis LLP

(57) ABSTRACT

This disclosure provides, among other things, a method for processing a membrane comprising rolling circle amplification (RCA) products. In some embodiments, this method may comprise: (a) obtaining a porous capillary membrane that comprises fluorescently labeled RCA products that are in or on the membrane; (b) depositing a curable polymer onto the membrane; and (c) curing the curable polymer to encapsulate the RCA products in a solid. In some embodiments, the curable polymer may be a silicone and may be transparent in its solid form. A kit for performing the method and a composition made by the method are also provided.

8 Claims, 3 Drawing Sheets

METHOD FOR PROCESSING ROLLING CIRCLE AMPLIFICATION PRODUCTS

CROSS-REFERENCING

This application is a divisional of U.S. application Ser. No. 15/724,573, filed on Oct. 4, 2017, which claims the benefit of provisional application Ser. No. 62/413,762, filed on Oct. 27, 2016, which application is incorporated by reference herein in its entirety.

BACKGROUND

Several nucleic acid-based diagnostic tests can be implemented by hybridizing probes to a nucleic acid sample, circularizing probes that hybridize to a target sequence, amplifying the circularized probes using rolling-circle amplification (RCA), and quantifying the number of RCA products.

In such methods, the RCA products can be quantified in a variety of different ways. For example, RCA products can, in theory, be quantified by labeling the RCA products, depositing the sample onto the surface of a glass slide, and counting the number of labeled products on the slide. However, simply placing a solution containing labeled RCA products on a glass slide, allowing the labeled RCA products to diffuse to the surface and then counting the number of labeled RCA products that have attached to the slide take several hours and not all of the labeled RCA products reach the slide and are counted. These problems can be largely solved by filtering the RCA products through a filter and then counting the number of labeled RCA products that have been captured by the filter. However, implementing such a method in a robust way can be challenging in some instances because many fluorescent labels can rapidly degrade when they are in contact with air. Further, RCA products can move around if the filter is wet. These challenges can make it difficult to implement such methods in a high throughput way, particularly when the sample has to be physically moved (e.g., inverted or rotated), the analysis cannot always be performed immediately, or a sample needs to be re-analyzed.

This disclosure is believed to provide a solution to these problems.

SUMMARY

This disclosure provides, among other things, a method for processing a membrane comprising rolling circle amplification (RCA) products. In some embodiments, this method may comprise: (a) obtaining a porous capillary membrane that comprises fluorescently labeled RCA products that are in or on the membrane; (b) depositing a curable polymer onto the membrane; and (c) curing the curable polymer to encapsulate the RCA products in a solid. In some embodiments, the curable polymer may be a silicone and may be transparent in its solid form. A kit for performing the method and a composition made by the method are also provided.

Encapsulating the RCA products in a solid (as opposed to using a liquid or no liquid), is believed to "fix" the RCA products, i.e., hold the RCA products in place, on the filter and also prevent the fluorescently labeled RCA products from being oxidized (i.e., degraded) by outside air. Thus, by encapsulating the RCA products in a solid, a filter comprising labeled RCA products can be rapidly moved in multiple directions (e.g., inverted, rotated or transported) and/or stored for an extended period of time (e.g., for weeks, months or even years). The present method may therefore facilitate the analysis of RCA products in a workflow that involves rapid multi-directional movement of the filter prior to analysis (e.g., by a robot) or in a workflow in which the RCA products cannot always be quantified immediately. In addition, the present method may be used in a workflow in which a filter may need to be re-analyzed after an extended period of time.

These and other potential features and advantages may become apparent in view of the following description.

BRIEF DESCRIPTION OF THE FIGURES

The skilled artisan will understand that the drawings, described below, are for illustration purposes only. The drawings are not intended to limit the scope of the present teachings in any way.

DETAILED DESCRIPTION

Figure 1:
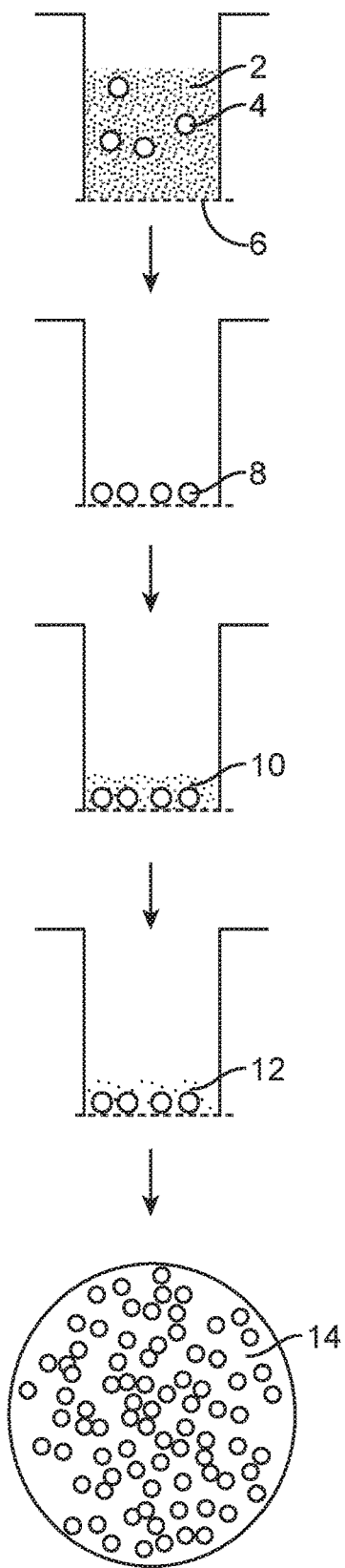
FIG. 1 schematically illustrates some of the steps of the present method.

Before the various embodiments are described, it is to be understood that the teachings of this disclosure are not limited to the particular embodiments described, and as such can, of course, vary. It is also to be understood that the terminology used herein is for the purpose of describing particular embodiments only, and is not intended to be limiting, since the scope of the present teachings will be limited only by the appended claims.

The section headings used herein are for organizational purposes only and are not to be construed as limiting the subject matter described in any way. While the present teachings are described in conjunction with various embodiments, it is not intended that the present teachings be limited to such embodiments. On the contrary, the present teachings encompass various alternatives, modifications, and equivalents, as will be appreciated by those of skill in the art.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present teachings, the some exemplary methods and materials are now described.

The citation of any publication is for its disclosure prior to the filing date and should not be construed as an admission that the present claims are not entitled to antedate such publication by virtue of prior invention. Further, the dates of publication provided can be different from the actual publication dates which can need to be independently confirmed.

As will be apparent to those of skill in the art upon reading this disclosure, each of the individual embodiments described and illustrated herein has discrete components and features which can be readily separated from or combined with the features of any of the other several embodiments without departing from the scope or spirit of the present teachings. Any recited method can be carried out in the order of events recited or in any other order which is logically possible.

All patents and publications, including all sequences disclosed within such patents and publications, referred to herein are expressly incorporated by reference.

Before describing exemplary embodiments in greater detail, the following meanings are set forth to illustrate the meaning and scope of the terms used in the description.

It must be noted that as used herein and in the appended claims, the singular forms "a", "an", and "the" include plural referents unless the context clearly dictates otherwise. For example, the term "a primer" refers to one or more primers, i.e., a single primer and multiple primers. It is further noted that the claims can be drafted to exclude any optional element. As such, this statement is intended to serve as antecedent basis for use of such exclusive terminology as "solely," "only" and the like in connection with the recitation of claim elements, or use of a "negative" limitation.

As used herein, the term "filtering" refers to the act of moving a liquid that contains analytes (e.g., rolling circle amplification products) through a filter such that some of the analytes are retained by the filter. In filtering, at least some of the liquid is transferred from one side of the filter to the other.

As used herein, the term "rolling circle amplification" or "RCA" refers to an isothermal amplification that generates linear concatemerized copies of a circular nucleic acid template using a strand-displacing polymerase. RCA is well known in the molecular biology arts and is described in a variety of publications including, but not limited to Lizardi et al (Nat. Genet. 1998 19:225-232), Schweitzer et al (Proc. Natl. Acad. Sci. 2000 97:10113-10119), Wiltshire et al (Clin. Chem. 2000 46:1990-1993) and Schweitzer et al (Curr. Opin. Biotech 2001 12:21-27), which are incorporated by reference herein.

As used herein, the term "rolling circle amplification products" refers to the concatamerized products of a rolling circle amplification reaction. As used herein, the term "fluorescently labeled rolling circle amplification products" refers to rolling circle amplification products that have been fluorescently labeled by, e.g., hybridizing a fluorescently labeled oligonucleotide to the rolling circle amplification products or other means (e.g., by incorporating a fluorescent nucleotide into the product during amplification).

As used herein, the term "porous capillary membrane" refers to a membrane that has relatively densely packed individual capillaries that span the thickness of the membrane, i.e., that go from one side of the membrane to the other, thereby allowing the passage of liquid, but not particles, from one side of the membrane to the other. Examples of porous capillary membranes include, but are not limited to, e.g., anodic aluminum oxide membranes (see below), nanochannel glass membranes, track etched membranes and polytetrafluoroethylene. Nanochannel glass membranes are made of glass and have a high density of uniform channels with diameters from 15 microns to 15 nanometers (see, e.g., Tonucci et al., Advances in Nanophotonics II, AIP Conference Proceedings, 2007 959: 59-71; Pearson et al., Science 1995 270: 68-70 and Tonucci et al., Science 1992 258: 783-785, as well as U.S. Pat. Nos. 5,306,661; 5,332,681; 5,976,444; 6,087,274; 6,376,096; 6,483,640; and 6,599,616, which are incorporated by reference). Track etched membranes are made of a transparent polymer (e.g., polycarbonate, polyethylene terephthalate or polyimide and the like) containing pores having a diameter in the range of 0.01 μm to 30 μm that have been made by a combination of charged particle bombardment (or irradiation) and chemical etching. Other porous membranes of interest include, but are not limited to amorphous fluoropolymers such as NAFION™, TEFLON AF™, FEFLON FEIP™, and CYTOP™ (DuPont Fluoroproducts, Fayetteville, N.C.). As would be recognized, a porous capillary membrane may have a surface (e.g., a coating or a chemically modified surface) that is different to the material from which the membrane is made. For example, the surface of a porous capillary membrane may have altered charge characteristics or altered hydrophobicity or hydrophilic characteristics. In some embodiments, the surface may be coated with amino silane, polylysine or another compound to provide a positive charge that helps retain the RCA products to the surface. Alternatively or in addition, the surface may have a thin layer of a metal (e.g., titanium, gold) deposited therein, which can be linked to other agents that modify the surface properties of the filter.

As used herein, the term "anodic aluminum oxide membrane" refers to a regular, self-organized nanoporous membranous structure that is produced when Al is anodized in certain acidic media. The interior diameter of the pores in the membrane, the distance between the centers of adjacent pores in the membrane, and the distance between the edges of adjacent pores in the membrane can be controlled by the voltage of the deposition, the type of acid, and other parameters. An anodic aluminum oxide membrane is virtually transparent when wet. Anodic aluminum oxide membrane, its properties, and how to make such membranes are reviewed in detail in a variety of publications including, but not limited to: Li et al (Chem. Mater 1998 10: 2470-2480), Santos et al (Trends on Analytical Chemistry 2013 44: 25-38), Ingham et al (Biotechnology Advances 30 2012 1089-1099) and Poinern et al. (Materials 2011 4: 487-526), which are incorporated by reference herein for those teachings. Anodic aluminum oxide membranes are commercially available under the trade name ANOPORE™ from, e.g., SPI Supplies (West Chester, Pa.) and from other vendors such as Sykera Technologies Inc. (Longmont, Colo.) and Sigma-Aldrich (St. Louis, Mo.) and can be purchased with a support ring.

As used herein, the term "area", in the context of an area of a membrane or an area of an image, refers to a contiguous or non-contiguous area. For example, if a method involves determining the amount of labeled RCA products in an area, e.g., counting the number of labeled RCA products in an area, the area in which the RCA products are quantified may be a single, contiguous space or multiple non-contiguous spaces.

As used herein, the term "imaging" refers to a process by which optical signals from the surface of an object are detected and stored as data in association with a location (i.e., a "pixel"). A digital image of the object can be reconstructed from this data. An area of a membrane may be imaged using a single image or one or more images.

As used herein, the term "individual labeled RCA products" refers to individual RCA molecules that are labeled.

As used herein, the term "determining the amount" refers to a method in which individually resolved RCA products are counted as well as methods that include measuring an aggregate signal from multiple RCA products. In methods that involve measuring the intensity of an aggregate signal, the individual RCA products do not need to be resolved. The amount of RCA products can be expressed using any suitable unit. In some cases, the amount of RCA products may be expressed as the number of individually resolved RCA products that have been counted.

As used herein, the term "counting" refers to determining the number of individual objects in a greater collection. In some embodiments, "counting" requires detecting separate signals from individual objects in a plurality (not a collective signal from the plurality of objects) and then determining how many objects there are in the plurality by counting the individual signals. In the context of the present methods, "counting" may be performed by determining the number of individual signals in an array of signals.

As used herein, the term "transparent" refers to a state in which an object is optically transparent at the wavelength being used. For fluorescence microscopy, "transparent" means that the object will be transparent to one or both of the excitation and emission spectra of a fluorophore. As will be described in greater detail below, certain membranes are transparent only when they have been wetted. Such membranes are considered transparent membranes even though the dry form of those membranes may not be transparent.

As used herein, the term "curable", in the context of a curable polymer, refers to a liquid polymer that can be made solid (i.e., "cured") via a cross-linking reaction. In some cases, a curable polymer can be made solid by addition of a curing agent (e.g., a second compound that causes or catalyzes crosslinking of the polymer). In some cases, curing can be initiated by an external stimulus (e.g., heat, humidity, or uv light).

As used herein, the term "solid" refers to the solid form of a curable polymer. A solid may be in the form of a semi-solid, such as a gel or rubber.

Other meanings of these and other terms may appear throughout the specification.

Prior to describing the present method in more detail, it is recognized that the present method can be implemented using any type of capture support that can act as a filter for RCA products. Such capture supports should have a low background signal at the wavelengths used in analysis and a pore size sufficient to allow rapid fluid flow-through of liquid and capture RCA products. Suitable capture supports may be made from porous organic or inorganic materials including solids such as porous metals, ceramics, homogeneous films (e.g., polymers) and heterogeneous solids (polymeric mixes, mixed glasses). Porous ceramic membranes can be made from inorganic materials (such as alumina, titania, zirconia oxides, recrystallized silicon carbide). See, e.g., the PamChip sold by Pamgene (The Netherlands), Wu et al, Nucleic Acids Res. 2004 32: e123 and Anthony et al Biotechniques. (2003) 34:1082-6, 1088-9. Exemplary porous polymer membranes can be made from cellulose acetate, nitrocellulose, cellulose esters (CA, CN, and CE), polysulfone (PS), polyether sulfone (PES), polyacrilonitrile (PAN), polyamide, polyimide, polyethylene and polypropylene (PE and PP), polytetrafluoroethylene (PTFE), polyvinylidene fluoride (PVDF) and polyvinylchloride (PVC). The description that follows below illustrates an implementation in which a porous capillary membrane is used. Porous capillary membranes are an example of a capture support that could be used. The following description illustrates the present method by example.

As summarized above, this disclosure provides a method for processing a membrane comprising rolling circle amplification (RCA) products. In some embodiments, this method may comprise: (a) obtaining a porous capillary membrane that comprises fluorescently labeled RCA products that are in or on the membrane; (b) depositing a curable polymer onto the membrane; and (c) curing the curable polymer to encapsulate the RCA products in a solid.

In some cases, the solid produced in (c) is transparent. In these embodiments, the solid form of the wetting agent may have a refractive index that is compatible with the membrane. For example, if anodic aluminum oxide membrane is used (which has a refractive index of approximately 1.72) then the solid form of the wetting agent may have a refractive index in the range of 1.2 to 1.8, e.g., 1.30 to 1.6. Silicones typically have refractive index of approximately 1.4 and are compatible with anodic aluminum oxide membranes. In some embodiments, the curable polymer should not shrink when it is cured.

Curable polymers include silicones, epoxys, as well as a variety of other plastics, many of which are transparent. The curable polymer may be formulated in a variety of different ways. For example, in some embodiments, the curable polymer may comprise a curing agent, e.g., catalyst for crosslinking the polymer or another compound that causes the polymer to cross-link. In some embodiments, the curable polymer may also contain a diluent. In these embodiments, the diluent may reduce the viscosity of the curable polymer, thereby allowing it to flow across the membrane to produce a layer of, e.g., 1 mm to 1 cm in thickness, e.g., 1 mm to 5 mm in thickness. Ideally, the curable polymer may have a viscosity in the range of 500 of 1200 mPa sec, although polymers having a viscosity outside of this range may be used in some circumstances. In some cases, the viscosity curable polymer may be adjusted so that the curable polymer, in liquid form, sits on top of and/or enters the pores of the filter, but does drain through the pores of the filter. In some cases, the curing step can be initiated by an external stimulus, e.g., heat, moisture or light (e.g., uv light) that causes the polymer to crosslink and solidify. Curing the curable polymer encapsulates the RCA in a solid at one side of the membrane.

In some embodiments, the membrane is an anodic aluminum oxide membrane. In these embodiments, the solid of (c) may act as a wetting agent that makes the membrane transparent. In these embodiments, the wetting properties of the solid may be provided by the cross-linked polymer itself or a diluent, e.g., an oil or solvent, that is trapped or cross-linked with in the solid. If a diluent (e.g., an oil) is used, then the diluent can potentially leak through the membrane over time, which can potentially interfere with imaging and/or autofocus after the sample has been stored. As such, diluents are less suitable for some applications. In these embodiments, the curable polymer may be a silicone. Silicone can be rapidly cured without shrinkage and without releasing substances that could affect the RCA products or fluorescence.

Silicone can be cured in a variety of different ways. In some embodiments, silicone can be cured in a platinum catalyzed reaction in which the crosslinker's Si—H groups react with the vinyl groups of a polymer to form a three-dimensional network. In another embodiment, silicone can be cured by peroxide curing. At elevated temperatures, peroxides decompose to form highly reactive radicals that chemically crosslink the polymer chains. In other embodiments, silicone can also be cured by condensation-curing, in which the terminal hydroxyl groups of the polymer react with a siloxane curing agent, releasing small, volatile compounds such as alcohol, acetic acid and amine. Silicone can also be cured using a tin catalyst. Other ways for curing silicone are known. In these embodiments, curable polymer deposited on the membrane may contain silicone and a curing agent (e.g., a platinum or tin catalyst, peroxide, or a siloxane) and an optional diluent (e.g., a silicone oil). In some embodiments, the method may comprise mixing the curable polymer (e.g., a silicone) with a curing agent (e.g., a platinum or tin catalyst, peroxide, or a siloxane) and, optionally, a diluent before depositing the curable polymer on the membrane.

In some embodiments, the solid may be made from a one or two component "RTV" silicone (i.e., room temperature vulcanization silicone), which is made from reactive oil-based polymers combined with strengthening mineral fillers. There are two types of room-temperature vulcanizing silicones: RTV-1 (a one-component system) hardens due to the action of atmospheric humidity, a catalyst, and acetoxysilane. Acetoxysilane, when exposed to humid conditions, will form acetic acid. The curing process begins on the outer surface and progresses through to its core. The product is packed in airtight cartridges and is either in a fluid or paste form. RTV-1 silicone has good adhesion, elasticity, and durability characteristics. The Shore hardness can be varied between 18 and 60. Elongation at break can range from 150% up to 700%. They have excellent aging resistance due to superior resistance to UV radiation and weathering. RTV-2 is a two-component product that, when mixed, cures at room-temperature to a solid elastomer, a gel, or a flexible foam. RTV-2 remains flexible from −80° C. to +250° C. Break-down occurs at temperatures above 350° C., leaving an inert silica deposit that is non-flammable and non-combustible. RTV silicones can be cured with a catalyst consisting of either platinum or a tin compound such as dibutyltin dilaurate.

SILGEL® 612 A/B and ELASTOSIL® RT 601 A/B (Wacker, Munich, GE) are examples of curable polymers that can be used in the method. SILGEL® 612 A/B is a pourable, addition-curing, RTV-2 silicone rubber that vulcanizes at room temperature to a very soft silicone gel. ELASTOSIL® RT 601 A/B is a pourable, addition-curing RTV-2 silicone rubber. If the ELASTOSIL® product is used, it may be diluted (e.g., 50:50, v:v) in a silicone oil, e.g., AK 35 silicon fluid, which is a linear, non-reactive polydimethylsiloxane with a viscosity of approx. 35 mm$^2$/s. This diluent may decrease the viscosity of the curable polymer. Both of these compounds, like many others, are transparent when they are cured and are able to wet anodic aluminum membranes, thereby making them transparent.

The method may be performed in a variety of different ways, one implementation of which is schematically illustrated in FIG. 1. With reference to FIG. 1, some embodiments of the method may include filtering a liquid sample 2 containing fluorescently labeled rolling circle amplification (RCA) products 4 through a porous capillary membrane 6 (e.g., an anodic aluminum oxide membrane). The filtering step concentrates the RCA results in RCA products 8 that are in or on the membrane. After any optional washing steps, the solution comprising a curable polymer 10 is deposited onto a porous capillary membrane, and the curable polymer is cured into a solid form to encapsulate the RCA products in a solid 12. In the illustrated embodiment, the next step involves detecting the RCA products while they are on the membrane. In some embodiments, this step may produce image 14 of the RCA products. As would be apparent, the detecting may be done using any suitable fluorescence detector, e.g., a fluorescence microscope, a scanner, using a high resolution CMOS or CCD detector or using a PMT or the like. Finally, the amount of labeled RCA products in the area of the membrane is determined, e.g., by counting individually resolved RCA products, or by measuring an aggregate signal, etc. This determination provides an estimate of the number of the labeled RCA products 4 in sample 2. The RCA products may be labeled before or after the filtering step.

As would be apparent, in any embodiment, the pores of the capillary membrane should be of sufficient size so as to prevent the RCA products from passing through the pores. For example, in embodiments, the pore diameter of the capillary membrane may be no more than 50% of the median diameter of the RCA products, while in some embodiments it may be no more than 20% of the median diameter of the RCA products, and in some embodiments no more than 10% of the median diameter of the RCA products. As such, in filtering the sample using the porous capillary membrane, the RCA products should remain on top of the membrane and should not fully enter or pass through the pores.

In some embodiments, the sample may contain at least a first population of RCA products and a second population of RCA products, wherein the first and second populations of labeled RCA products are distinguishably labeled. In these embodiments, the method may comprise determining the amount of the first labeled population of RCA products and the amount of the second labeled population of RCA products in an area of the membrane.

In some embodiments, a sample containing fluorescently labeled RCA products is placed into a container, e.g., a well that contains the membrane, e.g., as the bottom surface. The sample is concentrated, as described above, by applying pressure that draws the liquid phase of the sample through the membrane. This may be an active force (e.g., a centrifugal force, a negative pressure or a positive pressure) or a passive force (e.g., via capillary action (using blotting paper, for example) or evaporation). The RCA products are retained on the surface of the membrane in the form of an array at a density of, e.g., at least 10, at least 50, at least 100, at least 500, at least 1,000, at least 5,000, or at least 10,000/mm$^2$, then the curable polymer is added to the membrane and solidified. As noted above, the curable polymer may wet the membrane to make it transparent, thereby allowing the RCA products to be detected, e.g., imaged, transported and/or stored so they can be re-read if a positive result is obtained. In some embodiments, the array can be analyzed from either side of the membrane, e.g., through the membrane. As would be apparent, if the membrane is read from "above", i.e., from the same side as the RCA products, the membrane should be transparent. The analyzed area may contain at least 10, e.g., at least 100, at least 1,000, at least 5,000, at least 10,000, at least 20,000, at least 50,000, at least 100,000, or at least 200,000 or more RCA products.

If desired, the RCA products can be labeled while they are bound to the membrane and, in certain embodiments, the membrane may be washed, e.g., with water or an aqueous buffer that contains salt, after the array of labeled RCA products has been produced and prior to analysis. This washing step may reduce background because potential sources of background (e.g., labeled nucleotides or labeled oligonucleotides that are not hybridized to an RCA product) can be washed through the filter and are not associated with the filter at the time the filter is analyzed. If necessary, other reagents, e.g., anti-fade or reagents that enhance fluorescence or the like, can be added to membrane prior to depositing the curable polymer to decrease the background or increase the signal or the like. Likewise, if necessary, the labeled RCA products can be bound (covalently or non-covalently) to the membrane surface prior to depositing the curable polymer if necessary. Chemistries for linking biomolecules to a surface are well known and, in certain cases, the RCA products may be made using a modified nucleotide or a primer that has a group that is specifically reactive with the surface of the membrane, thereby ensuring that only the RCA products become attached to the surface.

The membrane used may be of any suitable thickness, e.g., in the range of 20 μm to 500 μm or 50 μm to 200 μm, as desired and, as noted above, may contain one or more support structures (e.g., a support ring) in order to maintain the integrity of the membrane during use. As noted above, the present method may be used in protocols that require accurate quantification of the number of RCA products in a sample, particularly a sample that has a variable concentration of RCA products (e.g., from 10 to 10M that can be at a relatively low concentration e.g., 5,000 to 1M RCA products in a volume of 50 µl to 200 µl or more) and the statistical resolution required to identify a difference can only be reached only by counting at least 1,000, at least 5,000, at least 10,000, at least 50,000, at least 100,000 or at least 200,000 or more of the RCA products. As will be described in greater detail below, the method has particular use in copy number analysis and in non-invasive prenatal testing applications.

Composition

A composition is also provided. In some embodiments the composition may comprise: (a) a porous capillary membrane (e.g., a porous anodic aluminum oxide membrane); (b) a plurality of fluorescently labeled RCA products on the membrane (e.g., at least 1,000, at least 5,000, at least 10,000, at least 20,000, at least 50,000, at least 100,000, at least 500,000, or at least 1M labeled RCA products; and (c) a layer of solid (e.g., a cured silicone) that encapsulates the fluorescently labeled RCA products. This layer of solid may be transparent in some embodiments and, as noted above, may wet the membrane to make it transparent. The labeled RCA products may be distributed across the surface of the membrane in a random manner at a density of, e.g., at least 10, at least 50, at least 100, at least 500, at least 1,000, at least 5,000, or at least 10,000/mm$^2$. In some embodiments, the solid may penetrate through at least the entrance of the pores of the membrane. In some embodiments, the composition may comprise at least two populations of fluorescently labeled RCA products on a surface of the membrane, where the different populations of fluorescently labeled RCA products are distinguishably labeled. Further details and variations of this composition may be found in the methods section of this disclosure.

Kits

Also provided by this disclosure are kits for practicing the subject methods, as described above. In some embodiments, a kit may contain at least: (a) reagents for producing fluorescently labeled RCA products (i.e., reagents for circularizing selected fragments in a sequence-specific manner and then performing rolling circle amplification of the circularized products, e.g., one or more restriction enzymes, a ligase, and one or more oligonucleotides that can act as a splint to circularize the products, a strand-displacing polymerase for amplifying the circularized products by RCA, one or more labeled oligonucleotides for labeling the RCA products, etc.); (b) a porous capillary membrane, e.g., a porous anodic aluminum oxide membrane; and (c) a curable polymer, e.g., a silicone. The kit may further comprise a curing agent in a separate container to the curable wetting agent. In some embodiments, the curable polymer and curing agent may be present in different barrels of a double barreled syringe that has a mixing tip. In some embodiments, the kit may also comprise a diluent, e.g., a silicone oil.

The various components of the kit may be present in separate containers or certain compatible components may be pre-combined into a single container, as desired. Further details and variations of components of this kit may be found in the methods section of this disclosure.

In addition to the above-mentioned components, the subject kits may further include instructions for using the components of the kit to practice the subject methods, i.e., instructions for sample analysis.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed.

Example 1

Multiplex Detection Methods

Materials and Methods

Devices: Aluminum oxide membranes with 20 nm pores were bonded to 96 well-plate super-structures that were custom produced.

In this multiplex experiment, mixtures of DNA from 2 cell lines were used as the genetic starting material. The cell line DNA contained either 2 copies of chromosome 21 (normal genetic makeup) or 3 copies of chromosome 21 (trisomy 21). DNA extracted from the cell lines was mixed in the following proportions 100:0, 95:5, 90:10, 0:100. Each DNA mixture was first digested using restriction enzymes, hybridized and ligated to a probe set, and subsequently enzymatically amplified by RCA as previously described (see WO2015083001 and WO2015083002). Two chromosome specific detection oligonucleotides (Atto 550 for chromosome 18, Atto 647 for chromosome 21) were added to each sample and allowed to hybridize thus fluorescently labeling the chromosome specific RCA products in each sample.

Following labeling, 100 µl samples were added to membrane-bottomed plates, and the plates were then placed on a vacuum manifold (Supleco part #66879-U). The samples passed through aluminum oxide membrane in approximately 90 seconds. The membrane-bottom plate was washed twice with 400 ul 0.5×SSC, then allowed to dry. Three hundred microliters of Wacker silgel 612/fixative was then applied to each well to make them transparent and to fix the RCA products to the membrane.

Imaging was done on an Olympus X81 microscope with a 20× objective and a Hamamatsu Orca 4.0lt camera. Imaging was done by tiling 10×10 images to cover the entire bottom of each well. Images were analyzed and RCA products counted using in-house purpose-built software.

Results

Figure 2:
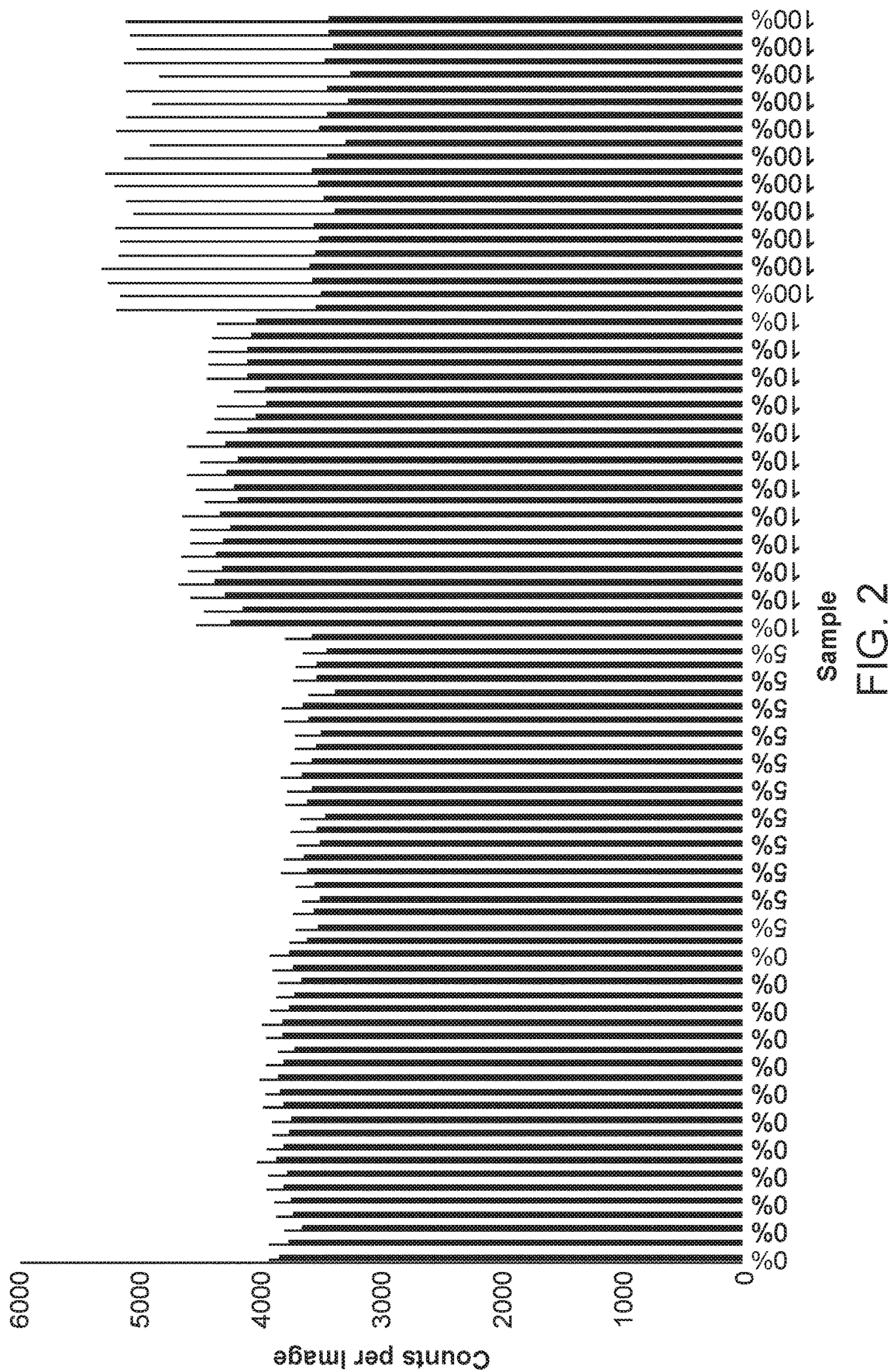
FIG. 2 is a histogram showing some of the results of the experiments described in Example 1.
Figure 3:
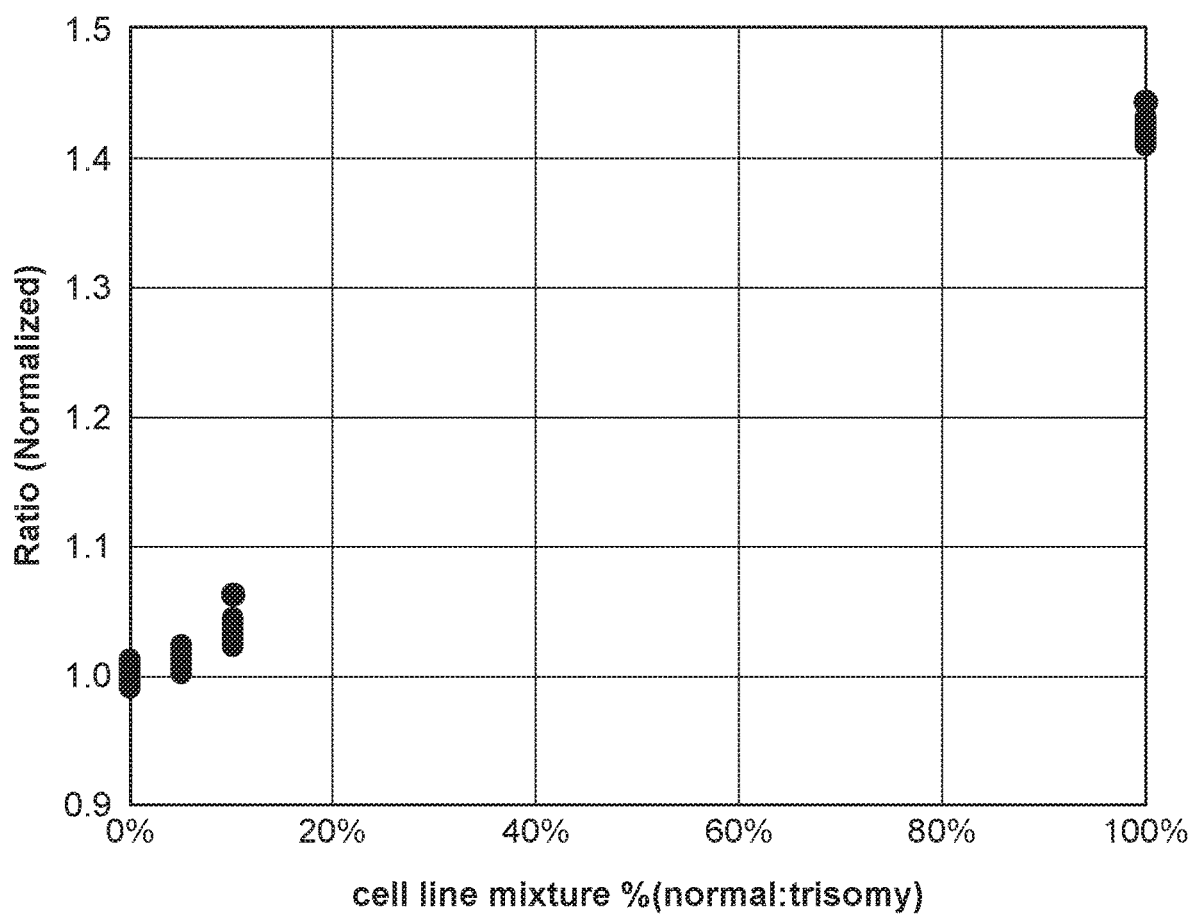
FIG. 3 is a plot of the ratios between the counts for two channels relative to the cell line mixture composition.

The results are summarized in FIG. 2. Average counts per image for all 91 samples included in the experiment ranged from 3000 to slightly over 5000 counts per image. The histograms clearly show a difference in proportion of counts between the 550 and 647 channels in the 0:100 ratio mixture (last 22 replicates), however it is more difficult to discern, from the figure alone, the proportion differences in the 0, 5, & 10% samples. FIG. 3 is a plot of the ratio between the counts for the two channels against cell line mixture composition. In this graph the trend is clearly represented, exemplifying the relative ratio shift in counts that follows the proportion of input cell line DNA samples.

The data demonstrates that deposition on the aluminum oxide membrane results in roughly 4 times higher counts than when deposited on the glass plate for the same 90 second time interval. If we increase the incubation time to 16 hours for the glass plate, the result is an increase of RCA products being detected on the glass plate, however still 2.5 times fewer than observed at 90 seconds on the aluminum oxide.

EMBODIMENTS

Embodiment 1. A method for processing a membrane comprising rolling circle amplification (RCA) products, comprising:
(a) obtaining a porous capillary membrane that comprises fluorescently labeled RCA products that are in or on the membrane;
(b) depositing a curable polymer onto the membrane; and
(c) curing the curable polymer to encapsulate the RCA products in a solid.

Embodiment 2. The method of embodiment 1, wherein the solid produced in step (c) is transparent.

Embodiment 3. The method of any prior embodiment, wherein the curable polymer of step (b) comprises a curing agent.

Embodiment 4. The method of any prior embodiment, wherein the curable polymer of step (b) comprises a diluent to reduce viscosity.

Embodiment 5. The method of any prior embodiment, wherein the membrane is an anodic aluminum oxide membrane, and wherein the solid of (c) has a wetting property that makes the membrane transparent.

Embodiment 6. The method of embodiment 5, wherein the curable polymer is a silicone.

Embodiment 7. The method of embodiment 6, wherein the silicone is mixed with a curing agent and, optionally, a silicone oil diluent.

Embodiment 8. The method of any prior embodiment, wherein the curing step (c) is initiated by an external stimulus.

Embodiment 9. The method of embodiment 8, wherein the external stimulus is heat, moisture or light.

Embodiment 10. The method of any prior embodiment, wherein the fluorescently labeled RCA products are made by:
filtering the RCA products through the membrane to produce RCA products that are in or on the membrane; and
fluorescently labeling the RCA products either before or after the filtering.

Embodiment 11. The method of any prior embodiment, wherein the method further comprises
(d) quantifying the number of the individual labeled RCA products in an area of the membrane, thereby providing an estimate of the number of the labeled RCA products in the sample.

Embodiment 12. A kit comprising:
(a) reagents for producing fluorescently labeled RCA products;
(b) a porous capillary membrane; and
(c) a curable polymer.

Embodiment 13. The kit of embodiment 12, wherein the kit further comprises a curing agent, wherein the curing agent is in the same container as the curable polymer.

Embodiment 14. The kit of embodiment 12, wherein the kit further comprises a curing agent, wherein the curing agent and the curable polymer are in different containers.

Embodiment 15. The kit of any of embodiments 12-14, wherein the curable polymer is a silicone.

Embodiment 16. The kit of any of embodiments 12-15, wherein the porous capillary membrane is an anodic aluminum oxide filter.

Embodiment 17. A composition comprising:
(a) a porous capillary membrane;
(b) a plurality of fluorescently labeled RCA products on the membrane;
(c) a layer of solid that encapsulates the fluorescently labeled RCA products.

Embodiment 18. The composition of embodiment 17, wherein the solid wetting agent penetrates through the pores of the filter.

Embodiment 19. The composition of embodiments 17 or 18, wherein the filter is an aluminum oxide filter.

Embodiment 20. The composition of any of embodiments 17-19, wherein the solid wetting agent is a cross-linked silicone.

The invention claimed is:

1. A combination comprising:
   (a) fluorescently labeled rolling circle amplification (RCA) products;
   (b) a porous capillary membrane; and
   (c) a cured polymer;
   wherein RCA products are in or on the membrane and the cured polymer contacts the RCA products and encapsulate the RCA products in a solid.

2. The combination of claim 1, wherein the cured polymer of (c) is transparent.

3. The combination of claim 1, wherein the cured polymer of (c) is a cured silicone.

4. The combination of claim 1, wherein the membrane of (b) is an anodic aluminum oxide membrane.

5. The combination of claim 1, wherein the fluorescently labeled RCA products of (a) comprises at least 1,000 fluorescently labeled RCA products.

6. The combination of claim 5, wherein the fluorescently labeled RCA products are at a density of at least $1,000/mm^2$.

7. The combination of claim 5, wherein the fluorescently labeled RCA products are randomly distributed on the membrane.

8. The combination of claim 1, wherein the fluorescently labeled RCA products of (a) comprises at least two populations of distinguishably-labeled RCA products.

* * * * *